United States Patent [19]

Ehret

[11] Patent Number: 6,159,724

[45] Date of Patent: *Dec. 12, 2000

[54] PROCESS FOR PREPARING CULTURE MEDIUMS FOR CULTURING YEASTS AND LACTIC ACID BACTERIA

[75] Inventor: Aloyse Ehret, Blotzheim, France

[73] Assignee: Agrano AG, Allschwil, Switzerland

[*] Notice: This patent is subject to a terminal disclaimer.

[21] Appl. No.: 08/904,745

[22] Filed: Aug. 1, 1997

Related U.S. Application Data

[63] Continuation of application No. 08/441,245, May 15, 1995, abandoned.

[30] Foreign Application Priority Data

May 27, 1994 [EP] European Pat. Off. .............. 94810305

[51] Int. Cl.⁷ .............................. A21D 2/00; C12N 1/00; C12N 1/20; C12N 1/14
[52] U.S. Cl. .................... 435/252.1; 426/18; 426/27; 435/252.4; 435/252.9; 435/255.1; 435/255.2; 435/255.4; 435/256.8; 435/822; 435/885; 435/857; 435/942
[58] Field of Search ........................ 435/240.3, 240.31, 435/240.54, 252.1, 255.1, 822, 252.4, 252.9, 255.2, 255.4, 256.8, 855, 857, 942; 426/18, 27

[56] References Cited

U.S. PATENT DOCUMENTS

| | | | |
|---|---|---|---|
| 3,868,307 | 2/1975 | Van Lanen et al. | 195/82 |
| 4,259,358 | 3/1981 | Dathie | 426/46 |
| 4,282,319 | 8/1981 | Conrad | 435/69 |
| 4,766,076 | 8/1988 | Sandine et al. | 435/253 |
| 4,908,443 | 3/1990 | Abe et al. | 540/221 |
| 5,231,017 | 7/1993 | Lantero et al. | 435/161 |
| 5,464,760 | 11/1995 | Tsai et al. | 435/139 |
| 5,700,684 | 12/1997 | Ehret | 435/255.2 |
| 5,702,943 | 12/1997 | Ehret | 435/253.6 |
| 5,776,526 | 7/1998 | Baensch et al. | 426/62 |

FOREIGN PATENT DOCUMENTS

| | | |
|---|---|---|
| 816571 | 12/1974 | Belgium . |
| 0093635 | 11/1983 | European Pat. Off. . |
| 0153057 | 8/1985 | European Pat. Off. . |
| 0229979 | 7/1987 | European Pat. Off. . |
| 0295358 | 12/1988 | European Pat. Off. . |
| 2353235 | 12/1977 | France . |
| 0372738 | 7/1932 | United Kingdom . |
| 91/04669 | 4/1991 | WIPO . |
| 9220777 | 11/1992 | WIPO . |

*Primary Examiner*—David M. Naff
*Assistant Examiner*—Deborah K. Ware
*Attorney, Agent, or Firm*—Tarolli, Sundheim, Covell, Tummino & Szabo L.L.P.

[57] ABSTRACT

A culture medium which is completely free of chemical additives and which can be used for the individual culture of yeast and of lactic acid bacteria or for the coculture of yeasts and lactic acid bacteria is prepared. The preparation of the medium is carried out by a process comprising making in a bioreactor a first medium using a dilute aqueous mixture containing a yeast autolysate and whole-meal or wheat germ, starch and gluten. Alpha-amylase enzymes and amyloglucosidase are added thereto for hydrolyzing the starch into a sugar. Furthermore proteolytic enzymes of food quality are also added for hydrolyzing gluten into aromatic peptides and free amino acids for microbial growth. The first medium is further sterilized and table salt may be added, however, no other chemical additives are ever added to the first medium. A second medium is prepared similarly as the first medium, however, in place of the second medium containing gluten it contains proteins for which the proteolytic enzymes of food quality are added for hydrolyzing the proteins into aromatic peptides and into free amino acids for microbial growth. The second medium is also further sterilized and table salt may be added, while no other chemical additives are added; and furthermore, the hydrolyses of the first and second mediums are carried out without pH regulation. The mediums are then combined to form a culture medium useful for making yeast cultures, lactic acid bacteria cultures and cocultures of yeast and lactic acid bacteria.

16 Claims, No Drawings

PROCESS FOR PREPARING CULTURE MEDIUMS FOR CULTURING YEASTS AND LACTIC ACID BACTERIA

This application is a continuation Ser. No. 08/441,245 filed on May 15 1995, now abandoned.

FIELD OF THE INVENTION

This invention refers to a process for preparing culture mediums which can be used for the individual culture of yeast and of lactic acid bacteria or for the coculture of yeasts and lactic acid bacteria, as well as to the use of said culture medium.

BACKGROUND OF THE INVENTION

Generally, baker's yeast is obtained from a culture medium consisting either of sugar molasses and chemical additives, or of cereals. However, said culture mediums necessitate a separation between the medium and the microorganism after the growth of the latter, in order to obtain a sufficient concentration of microorganisms permitting a panification under conditions which are compatible with an industrial production.

In the case of a so called "sour dough" panification, the production of the sponge necessitates successive precultures and a long adaptation of the microorganisms to the cereal environment, which both are incompatible with an industrial production.

SUMMARY OF THE INVENTION

A first object of the present invention is to eliminate said disadvantages of the prior art.

Another object of the present invention is to create culture mediums which can be used for the individual culture of yeast and of lactic acid bacteria or for the coculture of yeasts and lactic acid bacteria, which are free from any chemical additives, and which permit a direct use of the cultivated microorganisms for industrial panification.

The foregoing and other objects, advantages and features of the present invention can be attained by a process comprising the following steps:

preparing a diluted aqueous mixture comprising at least whole-meal and/or wheat germs as well as yeast autolysate (hereafter called "diluted mixture" for convenience);

completely hydrolyzing the starch in this mixture into fermentable sugars by the action of at least one alpha-amylase and of at least one amyloglucosidase;

gently hydrolyzing in this mixture at least part of the gluten by means of proteolytic enzymes of food quality into aromatic peptides and into free amino acids, and this in sufficient quantity to assure, when using the culture medium, a maximum microbial growth; and sterilizing the obtained product.

DESCRIPTION OF PREFERRED EMBODIMENTS

Preferably, said diluted mixture contains also table salt, and particularly sea salt.

The process according to the present invention, depending on the composition of said diluted mixture, produces two different mediums, one called "base medium" and the other called "culture medium".

Preferably, the proteolytic enzymes comprise at least two different proteases, one being an endoprotease, and the other being an exoprotease.

Preferably, the hydrolyses is executed in a bioreactor without pH regulation.

The culture mediums obtained according to the present invention are especially useful for the culture of yeasts, in particular those of the type *Saccharomyces cerevisiae*, preferably isolated from a natural sponge, and more particularly of the strain *Saccharomyces cerevisiae* steineri DSM 9211.

Likewise, the culture mediums obtained according to the present invention are especially useful for the mixed culture and/or the sequential culture of yeasts with lactic acid bacteria, particularly of yeasts of the type *Saccharomyces cerevisiae*, preferably isolated from a natural sponge, and of lactic acid bacteria of the genera Lactobacillus, Pediococcus and/or Leuconostoc, preferably also isolated from a natural sponge. They particularly allow the culture of the strain *Saccharomyces cerevisiae* steineri DSM 9211 in a mixed culture and or a sequential culture with one or several of the strains *Lactobacillus plantarum* DSM 9208, *Lactobacillus brevis* DSM 9209, *Pediococcus pentosaceus* DSM 9210 and *Leuconostoc mesenteroides* DSM 9207.

In this case, the yeast strain is discontinuously grown in a bioreactor in a mixed and/or sequential culture alimented with one or several bacterial strains, depending of the nature of the pacification product which is finally to be produced.

This permits the control of the metabolism of each microorganism, thus permitting to act on the concentration of the final metabolites, particularly ethanol, lactic acid and acetic acid. The choice of the microorganismes, based on their metabolic particularities, especially on the homofermentative or heterofermentative ways, and particularly the regulation of the depending enzymatic activity of pyruvate oxydase oxygen (cf.: Frey, Le Lait 1992) enables control of the concentration of acetic acid in the final mixture in a very delicate manner.

In the coculture process, part of the final metabolites produced by one of the microbial species is reused by the other species, which influences the final organoleptic qualities (reused lactic acid and production of acetic acid).

The sequential system permits to eventually delay the bringing into action of one microorganism with respect to another, or others, respectively.

The process according to the present invention offers several possibilities for carrying through the mixed and/or sequential culture:

(1) To culture simultaneously one or several yeasts and one or several lactic acid bacteria strains (mixed culture).

(2) To culture first one or several yeasts for a given period of time, and to culture thereafter, in the obtained yeast culture, one or several lactic acid bacteria strains (sequential culture).

The culture of the lactic acid bacteria itself may by simultaneous (i.e. several strains are inoculated at the same time), or may be delay (i.e. a first strain is set in a coculture with the yeast or several yeasts at time $t_1$, then a second strain is introduced at time $t_2 \ldots t_x$).

In the same way, the culture of the lactic acid bacteria can precede the start of the coculture with the yeast, or several yeasts, respectively.

The following Table summarizes these possibilities in a simplified scheme.

Abbreviation: L.a.b.=Lactic acid bacteria

TABLE

| Culture Types | | | | |
|---|---|---|---|---|
| (1) $t_0$ | | | | $t$ |
| Yeasts (s) | | | | Harvest |
| (2) (a) $t_0$ | $t_1$ | | | $t$ |
| Yeasts (s) | L.a.b. | | | Harvest |
| (b) $t_0$ | $t_1$ | $t_2$ | | $t$ |
| Yeasts (s) | L.a.b.1 | L.a.b.2 | | Harvest |
| (c) $t_0$ | $t_1$ | | | $t$ |
| Yeasts (s) L.a.b.1 | L.a.b.2 | | | Harvest |
| (d) $t_0$ | $t_1$ | $t_2$ | | $t$ |
| Yeasts (s) L.a.b.1 | L.a.b.2 | L.a.b.3 | | Harvest |
| (e) $t_0$ | $t_1$ | | | $t$ |
| L.a.b. | Yeasts (s) | | | Harvest |

In all cases, the use of the said microorganisms, cultivated in the culture medium prepared according to the present invention, allows in the industrial panification the generation of characteristic organoleptic qualities.

EXAMPLE 1

Ingredients Used for the Preparation of the Culture Mediums

The following ingredients are used for the preparation of the culture mediums described hereafter:

Wheat kernels, ground before use to safeguard the integrity of the nutritional values. A typical analysis of the product is as follows:
water approximately 13%,
total proteins approximately 12%,
carbon hydrates approximately 69%,
total lipids approximately 2%,
starch approximately 59%,
ash 1.5%.

Wheat germs, ground at low speed with controlled reduced heating. A lipid content from 11 to 12% and a starch content of less than 10% should be retained in order to guarantee the quality of the product. A typical analysis of the product is as follows:
water approximately 13%,
total proteins approximately 31.5%,
carbon hydrates approximately 25%,
total lipids approximately 11%,
starch approximately 8%,
ash 5%.

Yeast autolysate of food quality providing the medium with vitamins and amino acids. A typical analysis of the product is as follows:
water approximately 3.5%,
total proteins approximately 50.5%,
carbon hydrates approximately 32%,
total lipids approximately 5%,
starch approximately 1.5%,
ash 7.5%.

Sea salt

Industrial water.

EXAMPLE 2

Preparation of Milieu Called "Dosage Medium"

8 liters of water, 1660 grams of ground wheat kernels, 1000 grams of wheat germs, 100 grams of yeast autolysate, 30 grams of sea salt, and 1 milliliters of an alpha-amylase solution (16 unites RAU/gram of starch to be hydrolyzed) are mixed in a bioreactor of a volume of 15 liters.

Thereafter, the mixture is heated to 85° C. for 20 minutes and then cooled to 75° C. Thereafter, 2 milliliters of the same enzyme are added. The temperature is maintained for 20 minutes.

The mixture is cooled to 60° C. Then, 50 milliliters of a solution of amyloglucosidase (16,700 AGI/milliliter) are added. The action of the enzyme is maintained for 90 minutes. The mixture is cooled to 50° C. and subjected to the hydrolysis by two specific proteases, the first one being purified and fractionated papaine, and the second one being fractionated pancreatine.

1.5 milliliters of the first protease per kilogram of flour and 2.3 grams of the second protease per kilogram of flour are used. The action of the proteases lasts 220 minutes.

The obtained culture medium is sterilized at 120° C. for 20 minutes. This medium, which is perfectly stable is stored at +4° C.

At no time during the preparation of the medium are any chemical additives involved. The final pH of the medium is about 6.0, for example 5.5 to 6.5.

The addition of alpha-amylase in two lots to the medium called "dosage medium" avoids the irreversible gelatinisation of the starch at the moment when the temperature raises above 65° C.

EXAMPLE 3

Preparation of the Medium Called "Base Medium"

This medium serves for the inoculation called in technical terms "tank bottom" in the production system of the biomass according to the process of the discontinued alimented culture (feed batch).

10 liters of water, 500 grams of wheat germs, 70 grams of yeast autolysate and 30 grams of sea salt are mixed in a bioreactor.

The medium is subject to hydrolysis by alpha-amylase (2 milliliters/kilogram of wheat germs) for 20 minutes at 75° C., thereafter to the action of the above-mentioned two specific proteases, i.e. purified and fractionated papaine and fractionated pancreatine, at 50° C. for 240 minutes. The medium is stored at +4° C.

At no time during the preparation of the medium are any chemical additives involved. The final pH of the medium is about 6.0, for example 5.5 to 6.5.

EXAMPLE 4

Analysis of the Liberated Sugars

For analysis, the liberated sugars are measured by high performance liquid chromatography, and the amino acids liberated by the hydrolysis under the action of the protease are measured by means of the ninhydrine reagent (S. Moore and W. H. Stein, J. Biol. Chem. 176, 367, 1948).

The obtained average values are as follows:
Dosage Medium (Example 2):

glucose approximately 86.5 grams/liter, maltose approximately 11 grams/liter, amino acids approximately 9 grams/liter.

Base Medium (Example 3):

glucose approximately 6 grams/liter, maltose approximately 12.5 grams/liter, amino acids approximately 6.5 grams/liter.

EXAMPLE 5

Use of the Culture Mediums for the Culture of Yeast 5 liters of a base medium, prepared according to Example 3 above, are introduced into a 15 liter bioreactor, having an useful capacity of 10 liters.

A strain of yeast identified as *Saccharomyces cerevisiae steineri*, and deposited with the German Collection of Microorganisms (DMS) under No. 9211, is added to this base medium. The strain had been cultivated on the dosage medium prepared according to Example 2 above.

The strain is stored at −80° C. on a cereal base containing glycerol. The strain is reisolted on the solid cereal base, and is kept on the same medium by successive reinoculation every 15 days.

An isolated colony is inoculated into the liquid cereal medium. A second culture is made with 20 milliliters of the first one in an Erlenmeyer of 500 milliliters, containing 200 milliliters of the cereal medium. The cellular density obtained after 16 hours of culture under agitation is $3.0 \cdot 10^8$ cells per milliliter. A third culture is prepared from the second one with 600 milliliters of the previous culture. The cellular density obtained after 8 hours at 30° C. is $2.5 \cdot 10^8$ cells per milliliter. The glucose is entirely metabolized, and the measured ethanol content is about 25 grams/liter.

600 milliliters of this yeast culture in its exponential phase are added to said 5 liters of the base medium. The mixture is continuously alimented with dosage medium. The temperature is maintained at 30° C. The pH, which is continuously measured, is not regulated, and the $pO_2$ is kept above 10%.

The alimentation speed is determined by two parameters which are essential for the good course of the process:
(a) The Parameter Ethanol Concentration of the Culture Medium:

Yeast is a microorganism capable of multiplying in aerobiose and/or in anaerobiose. The aerobic metabolism is favorable to the growth of the biomass, whereas the anaerobic metabolism leads to the production of ethanol and of secondary derivatives which are searched for their organoleptic qualities. The process according to the present invention allows for control of the metabolic flow between these two extreme ways, permitting a good growth and therefore obtaining a final biomass which is capable of being used in the direct panification under "industrial" time conditions.

The production of ethanol indicates a metabolic flow into the anaerobic pathway.

In the described process, the ethanol concentration is systematically examined and maintained between 0.5 and 10 grams/liter. If the ethanol concentration drops below the limit of 0.5 grams/liter, the alimentation speed of the dosage medium is raised. On the other hand, the alimentation speed of the dosage medium is reduced if the ethanol concentration exceeds the limit of 10 grams/liter.
(b) The Aeration of the Culture Medium:

This parameter is continuously determined by continuously measuring dissolved oxygen, and is controlled in two ways, i.e. by controlling the entry of air into the bioreactor and/or by diminishing the rotation speed of two agitator blades of the Rushton type (Size of the blades: one half of the diameter of the bioreactor), allowing the control of $O_2$ the transfer.

In the described process, the partial pressure of $O_2$ is kept above 10%. The agitation speed varies between 500 to 1200 rpm, and the exit of sterile air is from 0 to 30 liters/minute.

Under the described conditions, the culture is fed during 16 hours. The total alimentation during this period is 4 liters. The cellular density of the yeast reaches $2 \cdot 10^9$ cells per milliliter (Density at start: $2.5 \cdot 10^7$ cells per milliliter).

The obtained culture is rapidly cooled to 3° C. and can then be kept without noticeable loss of its qualities for 21 days.

Variant:

A postfermentation on flour in the ratio of 50 to 300 grams/liter of ferment for 6 hours at 20° C., followed by cooling to 3° C., allows a storage during 30 days and the obtaining of a panification product having the organoleptic qualities of the "sponge" type.

Panification:

The liquid ferments (obtained directly from the bioreactor or after postfermentation) are used directly in a concentration of 20% (weight of flour/volume of ferment) for making a traditional dough from flour, water and salt.

Variant:

The ferments are centrifuged. The reduction of their water content raises their stability and allows to considerably diminish the concentration in the panification process. Thus, a centrifugation at 8,500 g (gravity) makes it possible to obtain a ferment containing 75% of water, which can be used in a concentration of 6 to 8% in the panification mixture.

The density of the obtained breads is identical with that of bread obtained by using the traditional pressed yeast (cultivated on sugary molasses) and used in a concentration of 2 to 3% on the weight of flour.

EXAMPLES 6 to 8

Use of the Culture Mediums for the Mixed Culture of Yeast and Lactic Acid Bacteria Preliminary Remark The ultimate aim is to obtain a preparation composed of a mixed culture allowing the preparation of a bread which is comparable to a bread made with traditional sponge. The mixed microbial growth brings about numerous interactions of the type commensalism, mutualism and ammensalism between the strains involved. The process described hereafter tries to make a compromise in producing Lactobacilli in sufficient quantity to produce flavors and a characteristic acidity in the breads, and to secure a sufficient proportion of yeasts (rising agents) which guarantee a well aerated bread with good density without further addition of yeast.

EXAMPLE 6

The culture starts with the growth of yeast. 5 liters of the base medium and 600 milliliters of a culture of *Saccharo-*

*myces cerevisiae* in an Erlenmeyer are continuously introduced into a 15 liter bioreactor, having a useful capacity of 10 liter. The mixture is fed with the dosage medium, and the temperature is maintained at 30° C. The pH, which is continuously measured, is not regulated. At the start the pH is 6, and it goes to 4.0 to 5.0 at the end of the mixed culture, depending on the strain of lactic acid bacteria used. The ethanol content is maintained between 0.5 and 10 grams/liter, by submission of the alimentation of the dosage medium. The agitation is effected by means of two agitator blades of the Rushton type (Size of the blades: one half of the diameter of the bioreactor—Transfer coefficient: 600 mmoles $O_2$/liter—Agitation speed: 500 to 1,200 rpm—Exit of sterile air varying: from 0 to 30 liters/minute). Said air exit depends on the partial pressure of oxygen which is continuously measured by means of a $pO_2$ electrode (Ingold), and is kept above 10%.

The inoculation of a lactic acid bacteria, i.e. *Lactobacillus plantarum*, is made after 8 hours and may be used to adjust the concentrations of the various microorganisms and to influence thereupon the organoleptic qualities of the final product.

EXAMPLE 7

This example shows a coculture which consist, at the start, of a mixed culture of yeast and *Leuconostoc mesenteroides*. This mixed culture is followed for 8 hours. After these 8 hours a pre-culture of *Lactobacillus plantarum* is added. The final product is obtained after 18 hours.

EXAMPLE 8

This example shows a coculture of the same type as that of Example 7, but in this test *Leuconostoc mesenteroides* is replaced by *Lactobacillus brevis* at the start of the coculture. *Lactobacillus plantarum* is added after 8 hours.

It is interesting to note the increase in production of lactic acid as compared with Example 2 (2.40 grams/liter against 1.81 grams/liter).

The obtained cellular density ratios between yeasts and bacteria are 3 to $5 \cdot 10^9$ yeast to 3 to $5 \cdot 10^9$ bacteria.

The final culture is cooled to 3° C. as quickly as possible. It can be stored for 8 days without loosing its panification capacity. It is used in a concentration of 20% (weight/volume).

The taste of the "sour dough" of the breads is excellent.

The Leuconostoc mesenteroides strain has been deposited under the terms of the Budapest Treaty at the DSM-DEUTSCHE SAMMLUNG VON MIKROORGANISMEN UND ZELLKULTUREN GmbH depository located at Mascheroder Weg 1b, D-3812 Braunschweig on May 19, 1994 and has been given the accession number DSM 9207.

The complete taxonomic description for the *Leuconostoc mesenteroides* strain is as follows:

Taxomony of *Leuconostoc mesenteroides* DSM 9207
(Morphological and physiological characteristics)

| | |
|---|---|
| Characteristics of colony | Diameter of colony: |
| (2 days, MSR Agar) | 0.5 to 1 mm, grey, smooth |
| Cell form and length | Cocci to short-rod-shaped |
| (MRS Bouillon) | |

-continued

Taxomony of *Leuconostoc mesenteroides* DSM 9207
(Morphological and physiological characteristics)

| | |
|---|---|
| Lactic acid configuration | D |
| Growth at 15° C. | Reaction positive |
| Growth at 45° C. | Reaction negative |
| End pH in MRS Bouillon | 4.2 |
| Gas formation out of glucose | Reaction positive |
| Aminonia out of arginine | Reaction negative |
| Diamino pimelic acid | Reaction negative |

The *Lactobacillus plantarum* strain has been deposited under the terms of the Budapest Treaty at the DSM-DEUTSCHE SAMMLUNG VON MIKROORGANISMEN UND ZELLKULTUREN GmbH depository located at Mascheroder Weg 1b, D-3812 Braunschweig on May 19, 1994 and has been given the accession number DSM 9208.

The complete taxonomic description for the *Lactobacillus plantarum* strain is as follows:

Taxonomy of *Lactobacillus plantarum* DSM 9208
(Morphological and physioiogical characteristics)

| | |
|---|---|
| Characteristics of colony | Diameter of colony: |
| (2 days, MSR Agar) | >1 mm, white, smooth |
| Cell form and length | Rod-shaped, different |
| (MRS Bouillon) | lengths, single to chains |
| Lactic acid configuration | DL |
| Growth at 15° C. | Reaction positive |
| Growth at 45° C. | Reaction positive |
| End pH in MRS Bouillon | 3.4 |
| Gas formation out of glucose | Reaction negative |
| Ammonia out of arginine | Reaction negative |
| Diamino pimelic acid | Reaction positjve |

The *Lactobacillus brevis* strain has been deposited under the terms of the Budapest Treaty at the DSM-DEUTSCHE SAMMLUNG VON MIKROORGANISMEN UND ZELLKULTUREN GmbH depository located at Mascheroder Weg 1b, D-3812 Braunschweig on May 19, 1994 and has been given the accession number DSM 9209.

The complete taxonomic description for the *Lactobacillus brevis* strain is as follows:

Taxonomy of *Lactobacillus brevis* DSM 9209
(Morphological and physiological characteristics)

| | |
|---|---|
| Characteristics of colony: | Diameter of colony: |
| (2 days, MSR Agar) | >1 mm, grey, smooth |
| Cell form and length | Rod-shaped, different |
| (MRS Bouillon) | lengths, single to chains |
| Lactic acid configuration | DL |
| Growth at 15° C. | Reaction positive |
| Growth at 45° C. | Reaction slightly positive |
| End pH in MRS Bouilion | 4.4 |
| Gas formation out of glucose | Reaction positive |
| Ammonia out of arginine | Reaction positive |
| Diamino pimelic acid | Reaction negative |

The *Pediococcus pentosaceus* strain has been deposited under the terms of the Budapest Treaty at the DSM-DEUTSCHE SAMMLUNG VON MIKROORGANISMEN UND ZELLKULTUREN GmbH depository located at Mascheroder Weg 1b, D-3812 Braunschweig on May 19, 1994 and has been given the accession number DSM 9210.

The complete taxonomic description for the *Pediococcus pentosaceus* strain is as follows:

Taxonomy of *Pediococcus pentosaceus* DSM 9210
(Morphoiogical and physiological characteristics)

| Characteristics of colony | Diameter of colony: |
|---|---|
| (2 days, MSR Agar) | >1 mm, white, smooth |
| Cell form and length | Cocci, in tetrades, also |
| (MRS Bouilion) | at pairs |
| Lactic acid configuration | DL |
| Growth at 15° C. | Reaction positive |
| Growth at 45° C. | Reaction positive |
| End pH in MRS Bouillon, | 3.7 |
| Gas forination out of glucose | Reaction negative |
| Ammonia out of arginine | Reaction positive |
| Diamino pimelic acid | Reaction negative |

The *Saccharomyces cerevisiae* steineri strain has been deposited under the terms of the Budapest Treaty at the DSM-DEUTSCHE SAMMLUNG VON MIKROORGANISMEN UND ZELLKULTUREN Gmbh depository located at Mascheroder Weg 1b, D-3812 Braunschweig on May 19, 1994 and has been given the accession number DSM 9211.

The complete taxonomic description for the *Saccharomyces cerevisiae* steineri strain is as follows:

Taxonomy of *Saccharomyces cerevisiae* steineri strain
DSM 9211
(Morphological and physiological characteristics)

| Yeast Morphology Agar | Form of colony: |
|---|---|
| | Smooth, glossy, whole-edge, white |
| Malt Bouillon | Cell form: |
| | Oval-shaped, multipolarly sprouting |
| Cornmeal Agar | No pseudonycellium |
| Malt Agar, V8 Agar | Asci formation: |
| | 2 to 4 ascospores per ascus; ascospores being round and smooth, ascus formation directly out from the vegetative cell |

Assimilation and Fermentation
(Percentage of positively reacting isolates)

| Substrates | Fermentation | Assimilation |
|---|---|---|
| Glucose | 100 | 100 |
| Galactose | 100 | 100 |
| Saccharose | 100 | 100 |
| Maltose | 100 | 100 |
| Lactose | 0 | 0 |
| Raffinose | 0 | 100 |
| Starch | 0 | 0 |
| Melibiose | 0 | 0 |
| Nitrate | | 0 |
| Trehalose | 0 | 0 |
| Cellobiose | 0 | 0 |
| L-Arabinose | 0 | 0 |
| D-Xylose | 0 | 0 |

What is claimed is:

1. A process for preparing a culture medium which can be used to make yeast cultures, lactic acid bacteria cultures, and cocultures of yeast and lactic acid bacteria, said process comprising the steps of:

(a) making in a bioreactor a first medium by preparing a first dilute aqueous mixture comprising yeast autolysate and whole-meal or wheat germ, said first dilute aqueous mixture comprising starch and gluten;

adding at least one alpha-amylase and at least one amyloglucosidase to hydrolyze said starch in said first dilute aqueous mixture into fermentable sugar;

adding at least one proteolytic enzyme of food quality to hydrolyze at least part of said gluten in said first dilute aqueous mixture into aromatic peptides and into free amino acids in amounts effective to promote microbial growth; and sterilizing said first medium;

at no time any supplemental chemical additives being added to said first aqueous dilute mixture other than table salt;

(b) making in a bioreactor a second medium by preparing a second dilute aqueous mixture comprising yeast autolysate and wheat germ, said second dilute aqueous mixture comprising starch and proteins;

adding at least one alpha-amylase to hydrolyze said starch in said second dilute aqueous mixture into fermentable sugar;

adding at least one proteolytic enzyme of food quality to hydrolyze at least part of said proteins in said second dilute aqueous mixture into aromatic peptides and into free amino acids in amounts effective to promote microbial growth; and sterilizing said second medium;

at no time any supplemental chemical additives being added to said second dilute aqueous mixture other than table salt;

wherein hydrolyzing with the alpha-amylase, amyloglucosidase and proteolytic enzyme in (a) and with the alpha-amylase and proteolytic enzyme in (b) are effected without pH regulation; and (c) combining said first medium and said second medium to form said culture medium at a time when said culture medium is used to make yeast cultures, lactic acid bacteria cultures, cocultures of yeast and lactic acid bacteria.

2. The process of claim 1, wherein said first medium further comprises table salt.

3. The process of claim 1, wherein said first medium further comprises sea salt.

4. The process of claim 1, wherein said second medium further comprises table salt.

5. The process of claim 1, wherein said second medium further comprises sea salt.

6. The process of claim 1, wherein said proteolytic enzyme added in making said first medium comprises at least two proteases, a first protease being an endoprotease, and a second protease being an exoprotease.

7. The process of claim 1, wherein said proteolytic enzyme added in making said second medium comprises at least two proteases, a first protease being an endoprotease, and a second protease being an exoprotease.

8. A process for culturing yeast, comprising the steps of inoculating said culture medium prepared according to claim 1 with a yeast and growing said yeast therein.

9. The process of claim 8 wherein said yeast is *Saccharomyces cerevisiae*.

10. The process of claim 9 wherein said yeast is a strain of *Saccharomyces cerevisiae* isolated from natural sponge.

11. The process of claim 10 wherein said yeast strain is *Saccharomyces cerevisiae* steineri DSM 9211.

12. A process for culturing yeast and lactic acid bacteria, comprising the steps of inoculating said culture medium prepared according to claim 1 with a yeast and lactic acid bacteria and growing said yeast and said lactic acid bacteria therein.

13. The process of claim 12 wherein said culture medium is simultaneously inoculated with said yeast and said lactic acid bacteria, said yeast being *Saccharomyces cerevisiae* and said lactic acid bacteria is a genus selected from the group consisting of Lactobacillus, Leuconostoc and Pediococcus.

14. The process of claim 13 wherein said yeast is the strain *Saccharomyces cerevisiae* steineri DSM 9211 and said lactic acid bacteria is one or more strains selected from the group consisting of *Lactobacillus brevis* DSM 9209, *Lactobacillus plantarum* DSM 9208, *Leuconostoc mesenteroides* DSM 9207 and *Pediococcus pentosaceus* DSM 9210.

15. The process of claim 1 wherein said culture medium is sequentially inoculated with *Saccharomyces cerevisiae* and with a lactic acid bacteria of a genus selected from the group consisting of Lactobacillus, leuconostoc and Pediococcus.

16. The process of claim 15 wherein the *Saccharomyces cerevisiae* is *Saccharomyces cerevisiae* steineri DSM 9211, and the lactic acid bacteria is one or more strains selected from the group consisting of *Lactobacillus brevis* DSM 9209, *Lactobacillus plantarum* DSM 9208, *Leuconostoc mesenteroides* DSM 9207 and *Pediococcus pentosaceus* DSM 9210.

* * * * *